(12) United States Patent
Chen et al.

(10) Patent No.: US 8,333,999 B2
(45) Date of Patent: Dec. 18, 2012

(54) PROCESS FOR COMPREHENSIVELY UTILIZING STEAM EXPLODED RADIX PUERARIAE AND DEVICE THEREFOR

(75) Inventors: Hongzhang Chen, Beijing (CN); Xiaoguo Fu, Beijing (CN); Weidong Wang, Changsha (CN)

(73) Assignees: Institute of Process Engineering, Chinese Academy of Sciences, Beijing (CN); Hu Nan Qiangsheng Medicine Co., Ltd., Changsha (CN)

( * ) Notice: Subject to any disclaimer, the term of this patent is extended or adjusted under 35 U.S.C. 154(b) by 681 days.

(21) Appl. No.: 12/447,895

(22) PCT Filed: Jul. 27, 2007

(86) PCT No.: PCT/CN2007/002268
§ 371 (c)(1),
(2), (4) Date: Apr. 29, 2009

(87) PCT Pub. No.: WO2008/061418
PCT Pub. Date: May 29, 2008

(65) Prior Publication Data
US 2010/0068778 A1     Mar. 18, 2010

(30) Foreign Application Priority Data

Nov. 22, 2006 (CN) .......................... 2006 1 0114727
Nov. 22, 2006 (CN) .......................... 2006 1 0114728
Nov. 22, 2006 (CN) .......................... 2006 1 0114729
Nov. 22, 2006 (CN) .......................... 2006 1 0114730

(51) Int. Cl.
*A61K 36/00* (2006.01)

(52) U.S. Cl. ....................................... 424/725; 424/773
(58) Field of Classification Search .................. None
See application file for complete search history.

(56) References Cited

U.S. PATENT DOCUMENTS

| 2005/0233423 A1* | 10/2005 | Berka et al. ................ 435/101 |
| 2010/0159569 A1* | 6/2010 | Medoff et al. ................ 435/277 |
| 2010/0160616 A1* | 6/2010 | Goel ............................ 536/6.3 |

FOREIGN PATENT DOCUMENTS

| CN | 1343770 | * | 4/2002 |
| CN | 1107722 C | | 5/2003 |
| CN | 1179923 C | | 12/2004 |
| CN | 1216150 C | | 8/2005 |
| CN | 1219873 C | | 9/2005 |
| CN | 1247103 C | | 3/2006 |
| CN | 1254544 C | | 5/2006 |

OTHER PUBLICATIONS

Shi et al. Chemistry and Industry of Forest Products. Feb. 2007. vol. 27, No. 1, pp. 57-60.*

* cited by examiner

*Primary Examiner* — Christopher R. Tate
(74) *Attorney, Agent, or Firm* — Knobbe, Martens, Olson & Bear, LLP

(57) ABSTRACT

The invention provides a process for co-producing ethanol and Radix Puerariae flavones and utilizing Radix Puerariae fibers from Radix Puerariae by way of clean solid state fermentation, and the device used therein. The process comprises the following steps: providing Radix Puerariae as raw material; pretreating the Radix Puerariae raw material by steam explosion; producing and separating ethanol by continuous coupled solid state fermentation; filtering off fermentation residues; and extracting and purifying Radix Puerariae flavones from the filtrate. The process achieves an effective and comprehensive utilization of Radix Puerariae.

9 Claims, 2 Drawing Sheets

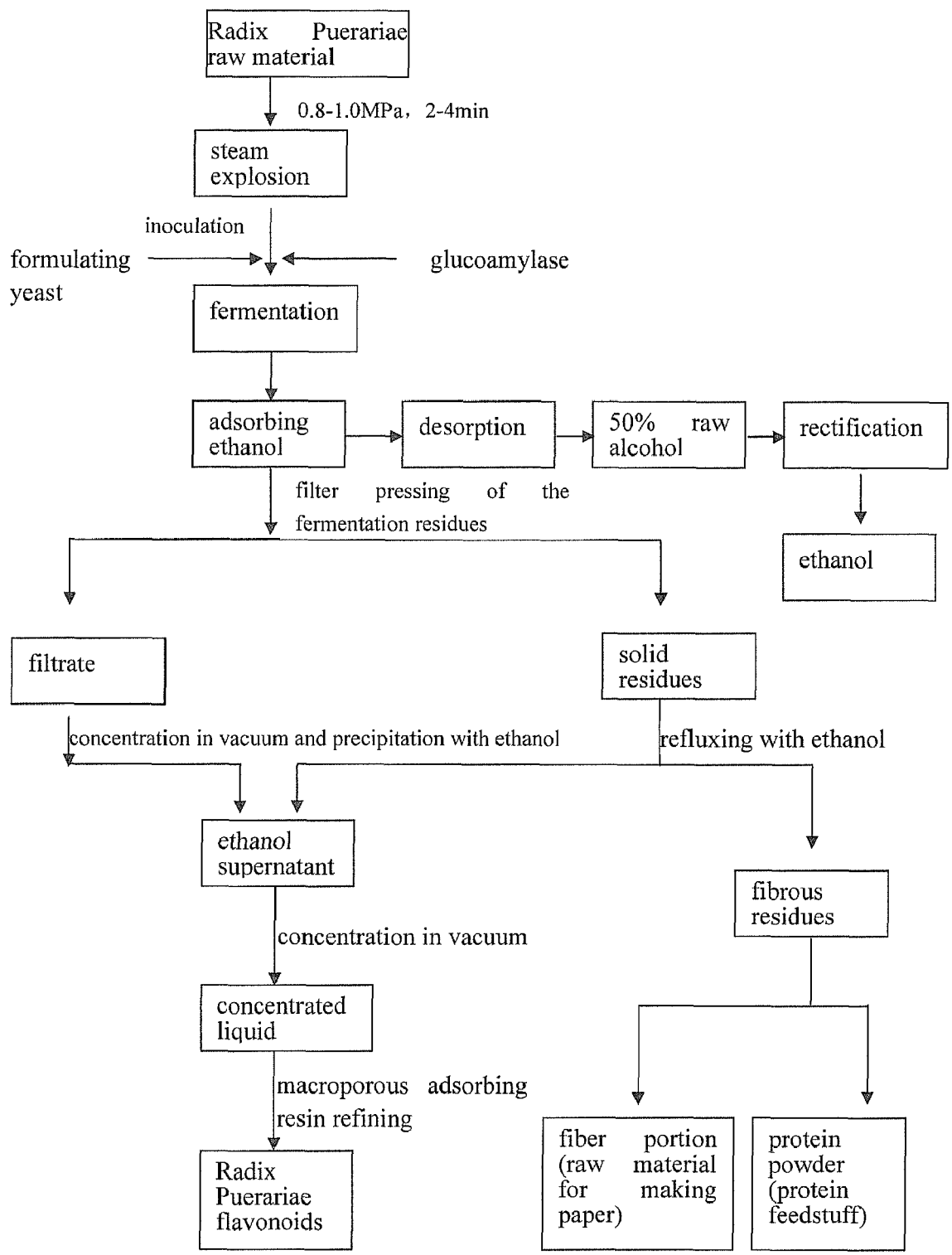
Figure 1: a process of a technical system for cleanly co-producing fuel ethanol, Radix Puerariae flavones and Radix Puerariae fibers by way of steam explosion and solid state fermentation of Radix Puerariae

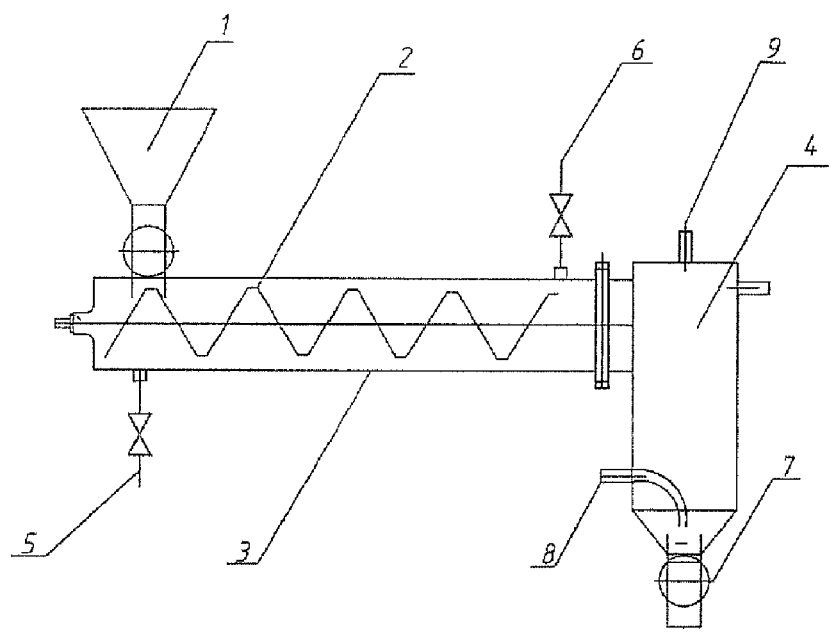
Figure 2: a figure of the continuous solid state fermentation device

PROCESS FOR COMPREHENSIVELY UTILIZING STEAM EXPLODED RADIX PUERARIAE AND DEVICE THEREFOR

This application is U.S. National Phase of International Application PCT/CN2007/002268, filed Jul. 27, 2007 designating the U.S., and published in Chinese as WO 2008/061418 on May 29, 2008, which claims priority to China Patent Applications Nos. 200610114729.7, 200610114728.2, 200610114730. X, and 200610114727.8, all of which were filed Nov. 22, 2006.

FIELD OF THE INVENTION

The present invention relates to a comprehensive utilization of plant resources, in particular, to a process for co-producing ethanol and Radix Puerariae flavones as well as utilizing Radix Puerariae fibers from Radix Puerariae, and also to a device used therein. The process comprises the following steps: first pretreating the raw material, i.e. Radix Puerariae, by steam explosion; producing fuel ethanol by continuously coupled solid state fermentation of Radix Puerariae starch; then extracting Radix Puerariae flavones and Radix Puerariae fibers from residues of the solid state fermentation, thereby accomplishing a graded transformation, comprehensive and clean utilization of Radix Puerariae.

BACKGROUND OF THE ART

Radix Pueraiae is the underground root of Pueraria, i.e. a perennial leguminous plant. As first recorded in *Shennong's Chinese Materia Medice*, Radix Puerariae was listed as a medium grade drug. Because of being rich in starch and isoflavones, Radix Puerariae is listed as both food and medicine by the Ministry of Health. There are more than 30 types of Pueraria in the world, which are distributed in China, Japan and southeast Asia. Among others, China, owning about 9 types of Pueraria and 2 mutations thereof, is the distribution center. Pueraria resources, including P. Lobata(will)Ohwi, P. Thomsoni Berth, P. edulis Pamp, P. Omeiensis Wang, and P. peduncularis Crah. ex Benth, etc. are all over the whole country, wherein P. Lobata(will)Ohwi and P. Thomsoni Berth are the most common Pueraiaee and have the highest resource amount. From a preliminary calculation, the growth area of Pueraria (including wild and cultivated) is approximately 400,000 hm$^2$, and the annual resource amount is over 1,500,000 tons. Radix Puerariae has become the focus of economic crop development project in many places in China, so its planting area is huge. The main components of Radix Puerariae are starch, cellulose, protein and Radix Puerariae isoflavones, and a small amount of fat, pectin, tannin and alkaloid, etc. are also contained. It is reported that the dry Radix Puerariae has 50-60% of starch, 9-15% of cellulose, 5-8% of raw protein and 3-5% of isoflavones. However, the fresh Radix Puerariae contains about 50-60% of water, and 18.5-27.5% of starch. Therefore, when considering extracting and utilizing Radix Puerariae flavones, i.e. the active pharmaceutical ingredient of Radix Puerariae, Radix Puerariae, as a starch-type energy source plant, may also be fermented to produce ethanol.

It has been reported that the extraction methods of Radix Puerariae flavonoids are water extraction method, alcohol extraction method, water extraction and alcohol precipitation method, alcohol extraction and water precipitation method, and the like. In 1970s, Radix Puerariae flavonoids were prepared by the Chinese Academy of Medical Sciences by means of a basic lead acetate precipitation method, i.e. a classic alcoholization method of flavones. Nevertheless, such method commonly causes heavy metal contamination, so it is not suitable to be used in pharmaceutical industry. Although the components of Radix Puerariae are very complicated, the pretreatment of Radix Puerariae for the extraction of flavones normally is only a simple mechanical crush.

The current application of Radix Puerariae's active ingredients is most likely in the processes for extracting Radix Puerariae starch and flavones, respectively. However, since Radix Puerariae contains a large amount of fibers, the mechanical crush requires a lot of energy, which leads to a complicated and incompleted starch extraction process and causes a waste of raw material. If the extracted Radix Puerariae starch is utilized to produce ethanol according to the process for producing ethanol from food-type starch, i.e. a process of steam boiling at a high or low temperature—gelatinizing—liquefying—saccharifying—liquid fermenting—primary distilling, wherein the energy depleted for steam boiling the raw material amounts to 30-40% of the total energy needed for the production of ethanol. Furthermore, such a process results in a great amount of highly concentrated organic waste water, which is not only likely to pollute the environment but also difficult to be used to extract Radix Puerariae flavones. Thus, for reasonably utilizing Radix Puerariae resources, it is required to make use of the characteristics of Radix Puerariae and develop a process suitable for co-producing ethanol and Radix Puerariae flavones as well as utilizing Radix Puerariae fibers from Radix Puerariae, thereby accomplishing a comprehensive utilization of Radix Puerariae resources.

DISCLOSURE OF THE INVENTION

An object of the invention is to provide a process for co-producing ethanol and Radix Puerariae flavones as well as utilizing Radix Puerariae fibers from Radix Puerariae. Such system comprises the following steps: first pretreating Radix Puerariae raw material by steam explosion; producing ethanol by performing a synchronously saccharified solid state fermentation of Radix Puerariae; and then extracting Radix Puerariae flavones and Radix Puerariae fibers from Radix Puerariae solid state fermentation residues, thereby carrying out a classified transformation and a comprehensive and clean utilization of Radix Puerariae components.

Another object of the invention is to provide a device used in the process.

In one aspect of the invention, a process for comprehensively utilizing Radix Puerariae is provided, the process comprising the following steps: 1) providing Radix Puerariae as raw material; 2) pretreating the Radix Puerariae raw material by steam explosion; 3) producing and separating ethanol by continuous coupled solid state fermentation; 4) filtering off fermentation residues; 5) extracting and purifying Radix Puerariae flavones from filtrates; and 6) classifying the filtered fermentation residues into a fiber portion and a protein portion.

In one embodiment of the invention, the steam pressure in step 2) is 0.5 to 1.0 Mpa, and the steam explosion time period is 2 to 4 min.

In another embodiment of the invention, glucoamylase, $(NH_4)_2SO_4$, $KH_2PO_4$ and activated yeast are added for the fermentation of Radix Puerariae in step 3). In an embodiment, the added amount of glucoamylase is 50~100 U/g Radix Puerariae; the added amount of $(NH_4)_2SO_4$ is 0.05~0.15 g/100 g Radix Puerariae; the added amount of $KH_2PO_4$ is 0.05~0.2 g/100 g Radix Puerariae; and the added amount of the activated yeast is 0.10~0.30 g yeast/100 g Radix Puerariae.

In another embodiment of the invention, the macroporous adsorbing resin model D-101, DS-401 or AB-8 is used to remove impurities.

In another aspect of the invention, it is provided a device used in the continuous coupled solid state fermentation, comprising an airlock 1, a screw 2, a horizontal pot 3, a vertical pot 4, a gas inlet 5 and a gas outlet 6 of the horizontal pot, a discharging airlock 7 of the vertical pot, a gas inlet 8 and a gas outlet 9 of the vertical pot (FIG. 2).

In an embodiment, said airlock is used in the feeding port of said horizontal pot 3 to ensure the isolation between the inside and the outside of the reactor while feeding.

In another embodiment, said screw 2 is installed inside the fermentation pot as a propulsive device for propelling the fermenting materials to move forward.

In a further embodiment, said airlock 7 is used in the discharging port at the bottom of said vertical pot, so as to ensure the isolation between the inside and the outside of the vertical pot while discharging.

In another aspect of invention, it is provided a process of continuous coupled solid state fermentation, comprising the following steps: solid materials continuously entering said horizontal pot 3 through said airlock 1; said screw 2 inside said horizontal pot slowly propelling the materials towards said vertical pot 4; and continuously discharging the materials through said airlock 7 at the bottom of said vertical pot, wherein biochemical processes such as enzymolysis, fermentation and separation etc. of the materials are completed during their continuous moving in and out.

In an embodiment, if a process involving enzymolysis followed by solid state fermentation (for the solid state fermentation types which requiring pre-enzymolysis) is used, the materials are subjected to the enzymolysis when a required temperature is maintained in said horizontal pot 3. While the enzymolysis is carried out, the materials are propelled towards the vertical pot 4 by the screw propeller 2. The propelling speed is adjusted, so that the residence time of the materials in said horizontal pot is identical to the time required for the enzymolysis. The materials are then subjected to water extraction or gas extraction. After the extraction is completed, the materials are discharged continuously through said airlock 7 in said discharge port.

In another embodiment, if a synchronous solid state fermentation process is used (for the fermentation types which requiring no pre-enzymolysis of the materials), the materials are subjected to the fermentation in said horizontal pot 3. While said fermentation is carried out, the materials are propelled towards said vertical pot 4 by said screw propeller 2. The propelling speed is adjusted so that the residence time of the materials in said horizontal pot is identical to the time required for the fermentation. The materials are then subjected to water extraction or gas extraction. After the extraction is completed, the materials are discharged continuously through said airlock in said discharge port.

In details, the invention relates to a process for co-producing ethanol and Radix Puerariae flavones and utilizing Radix Puerariae fibers from Radix Puerariae by way of clean solid state fermentation. Such process comprises the following steps: first pretreating the raw material, i.e. Radix Puerariae, by steam explosion; fermenting to produce fuel ethanol by a continuous coupled solid state fermentation of Radix Puerariae starch; then extracting Radix Puerariae flavones and Radix Puerariae fibers from residues of the solid state fermentation, and thereby carrying out a classified transformation, a comprehensive and clean utilization of Radix Puerariae. The steps are as follows:

1) pretreating by steam explosion: steam exploding Radix Puerariae under a steam pressure of 0.5-1.0 Mpa for 2-4 min;
2) producing ethanol by continuous coupled solid state fermentation;
   a) the steam exploded Radix Puerariae is placed in an antoclave and sterilized therein. The sterilization temperature is 121-125° C., and the sterilization period is 15-20 min. Steaming sterilization is used in the solid state fermentation reactor. Steam enters through the inlet 11 and exits through the outlet 12, maintaining 121-125° C. for more than 30 min. After the sterilized materials is cooled down to 30-35° C., glucoamylase, $(NH_4)_2SO_4$, $KH_2PO_4$ and the activated yeast are added under sterile conditions;
   b) after the motor of the airlock is turned on, the sterilely inoculated Radix Puerariae substrate is delivered slowly into the fermentation pot with a speed of 1 kg/10 h (the natural stacking density is approximately 400 g/L) through the feeding port 1. When the materials are fed for fermentation, $CO_2$ enters through the gas inlet 11 and replaces the air inside the pot. The temperature is maintained at 35±1° C. in the fermentation pot. The rotating speed of the screw is adjusted to ensure the residence time of the materials in the pot is about 60 h;
   c) gas extraction: while being fermented, Radix Puerariae substrate moves forward under the pushing action of the screw propeller and reaches the gas extraction pot 3 right after 60 h. The gas is circulated by the $CO_2$ entering through the gas inlet 13 at the bottom of the gas extraction pot. The gas speed is 2-10 L/min, and ethanol is carried away from the substrate;
   d) adsorption: the mixed gas of $CO_2$ and ethanol passes two active carbon absorbing columns 4, 5 in parallel (two adsorbing columns are in parallel. If one adsorbing column is measured to reach saturation using an ethanol concentration meter 16, the other adsorbing column may then be switched to). The ethanol contained in the mixture is adsorbed, and the remaining $CO_2$ is compressed and may be utilized repeatedly;
   e) desorption: when no ethanol is measured in the mixed gas by using the ethanol concentration meter 16, the adsorbing column is heated to 90° C., which permits the adsorbed ethanol to be desorbed off the active carbon absorbing column;
   f) recovering by condensation: the ethanol desorbed off the adsorbing column is brought into a condensation tube 6 by the air flow entering through the bottom of the adsorbing column. The ethanol is recovered and obtained after the condensation;
   g) post-treatment: after fermentation, the Radix Puerariae residue is discharged through the discharging airlock at the bottom of the gas extraction pot 15.
3) filter-pressing the Radix Puerariae residues discharged from the bottom of the gas extraction pot; adding 95% ethanol with a volume ratio of the filtrate to 95% ethanol to be 1:1.7~3.75, or adding absolute ethanol with a volume ratio of the filtrate to absolute ethanol to be 1:1.5~3.0; standing for 1-3 h followed by centrifugal separation;
4) adding ethanol with a concentration of 60-95% to the filtered residues obtained from the step 3 with a mass/volume ratio of the filtered residue to extraction solvent of 1:4~10; performing the extraction for 1 to 3 times under reflux when heated to a temperature of 50 to 80° C. for a total extraction time of 0.5-3 h; filtering the extraction liquid;

5) combining the centrifugal supernatant in step 3 and the extraction liquid filtered in step 4; recovering ethanol under a vacuum degree of -0.08 Mpa and at a temperature of 50° C.; loading the concentrated liquid onto a macroporous adsorbing resin; eluting the macroporous adsorbing resin first with water to remove the impurities and then with 10-70% ethanol to collect the ethanol eluent; after concentration, adding ethanol to render the alcohol concentration to reach 70-80%; filtering off the precipitate, concentrating the filtrate, extracting by adding n-butanol, recovering the n-butanol, concentrating, drying and obtaining the Radix Puerariae flavonoids extract;

6) directly hot-air drying the fibrous residues obtained after the extraction of Radix Puerariae flavones under reflux in step 4 until the water content reaches about 25%, followed by mechanically classifying into a fiber portion and a protein portion with a ratchet.

In one embodiment, the added amount of glucoamylase is 50~100 U glucoamylase per gram Radix Puerariae;

In another embodiment, the added amount of $(NH_4)_2SO_4$ is 0.05~0.15 g $(NH_4)_2SO_4$ per 100 g Radix Puerariae;

In a further embodiment, the added amount of $KH_2PO_4$ is 0.05~0.2 g $KH_2PO_4$ per 100 g Radix Puerariae;

In another embodiment, the added amount of yeast is 0.10~0.30 g yeast per 100 g Radix Puerariae;

In a further embodiment, the macroporous adsorbing resin model is D-101, DS-401 or AB-8.

For the above purposes, we measured some critical indexes for realizing the system of the invention, the results are shown as follows:

1. The Influence of Steam Explosion Pressure on Radix Puerariae

Radix Puerariae was steam exploded under a steam pressure of 0.5~1.0 Mpa for 2.5 min. The contents of water, water-soluble reducing sugar and water-soluble total sugar of Radix Puerariae as well as the yield of Radix Puerariae flavones after pretreatment under different steam explosion conditions were measured respectively. The results are shown in Table 1.

TABLE 1 the effect of steam explosion pressure on Radix Puerariae

| Steam explosion condition (Pa) | Initial water content % | Water % after steam explosion | Water-soluble reducing sugar % (based on dry Radix Puerariae) | Water-soluble total sugar % (based on dry Radix Puerariae) | The yield of flavones % (based on dry Radix Puerariae) |
|---|---|---|---|---|---|
| 0 | 72.3 |  | 12.670 | 17.433 | 1.433 |
| 0.5 | 72.3 | 83.03 | 15.440 | 23.144 | 1.748 |
| 0.6 | 72.3 | 78.65 | 16.147 | 24.534 | 0.902 |
| 0.7 | 72.3 | 76.23 | 17.443 | 24.728 | 0.838 |
| 0.8 | 72.3 | 76.93 | 25.021 | 31.908 | 1.164 |
| 0.9 | 72.3 | 75.18 | 19.710 | 19.892 | 1.322 |
| 1.0 | 72.3 | 79.67 | 22.552 | 23.741 | 1.603 |

As shown in Table 1, the effect of pre-treatment by steam explosion on Radix Puerariae was different under different steam pressures. Steaming increased the water content of Radix Puerariae after steam explosion. As the steam explosion pressure increased, the contents of water-soluble reducing sugar and water-soluble total sugar first increased and then decreased. The heating mechanical chemical action of the steam explosion broke cell walls of plant tissues, damaged structures of the solid material (i.e. Radix Puerariae), and raised the sugar concentration generated from the hydrolysis of Radix Puerariae starch. However, when the steam explosion pressure was further increased, the water-soluble sugar in the materials might be lost for undesired reactions. The amount of extracted Radix Puerariae flavonoids was closely related to the characteristics of the materials. The dextrinization level of Radix Puerariae starch was also different after the treatment under different steam explosion pressures, which directly affected the separation of Radix Puerariae flavones. Therefore, after the steam explosion treatment, the amount of extracted Radix Puerariae in the materials varied with the steam explosion pressure. Selecting a suitable pressure will increase the amount of extracted Radix Puerariae flavones. Based on the preliminary consideration of the steam explosion effect of Radix Puerariae, 0.8 Mpa was selected as the steam explosion pressure for the following experiments.

2. The Effect of Steam Explosion Pressure Holding Time on Radix Puerariae

According to the experiment concerning the effect of steam explosion pressure on Radix Puerariae, 0.8 MPa was selected as the steam explosion pressure in this experiment. The pressure was maintained for 2.0-4.0 min. The contents of water, water-soluble reducing sugar and water-soluble total sugar as well as the yield of Radix Puerariae flavones after different steam explosion pressure holding times were measured respectively. The results are shown in Table 2.

TABLE 2 the effect of steam explosion pressure on Radix Puerariae

| Steam explosion condition (Min) | Initial water content % | Water % after steam explosion | Water-soluble reducing sugar % (based on dry Radix Puerariae) | Water-soluble total sugar % (based on dry Radix Puerariae) | The yield of flavones % (based on dry Radix Puerariae) |
|---|---|---|---|---|---|
| 0 | 72.3 |  | 12.670 | 17.433 | 1.433 |
| 2.0 | 72.3 | 73.10 | 19.725 | 23.134 | 0.858 |
| 2.5 | 72.3 | 76.93 | 25.021 | 31.908 | 1.164 |
| 3.0 | 72.3 | 77.37 | 18.353 | 24.728 | 1.693 |
| 3.5 | 72.3 | 75.71 | 20.024 | 27.908 | 1.731 |
| 4.0 | 72.3 | 76.95 | 17.061 | 19.892 | 1.627 |

As shown in Table 2, the length of the steam explosion pressure holding time directly influenced the effect of the pretreatment on the materials. When the pressure was maintained at 0.8 MPa for 3.5 min, the contents of water-soluble reducing sugar and water-soluble total sugar as well as the amount of extracted Radix Puerariae flavones all reached a better level.

3. The Changes of Components of Radix Puerariae Before and after the Steam Explosion Treatment The main components of Radix Puerariae not only include starch and Radix Puerariae flavones, but also include approximately 10% raw fibers. Does the steam explosion treatment also affect these components? Therefore, we measured the Radix Puerariae components before and after steam explosion. The results are shown in Table 3. It was shown that before and after steam explosion, the component contents in Radix Puerariae varied dramatically. After the steam explosion treatment, the component of neutral detergents decreased by about 10%, i.e. from 70.7112% in the Radix Puerariae before steam explosion to about 60% in the steam exploded Radix Puerariae. The relative content of cellulose in Radix Puerariae did not change much, i.e. change from 8.17% before steam explosion to about 10% after the explosion. But the relative content of hemicellulose increased by about 30%, i.e. from 19.0253% to about 25.0%. The changing tendency of the relative content of lignin is not very clear, whereas after steam explosion, the relative content of ash increased from 0.8254% of the original Radix Puerariae to about 1.5%, i.e. almost doubled.

TABLE 3 the component changes of Radix Puerariae before and after steam explosion treatment (based on dry materials)

| Steam explosion condition | Neutral detergent % | hemicellulose % | cellulose % | lignin % | ash % |
|---|---|---|---|---|---|
| Original Radix Puerariae without steam explosion | 70.7112 | 19.0253 | 8.1784 | 1.2597 | 0.8254 |
| 0.5 * 2.5 | 48.1452 | 34.6056 | 9.9930 | 6.3731 | 0.8831 |
| 0.6 * 2.5 | 53.7033 | 31.9630 | 10.0056 | 3.4758 | 0.8522 |
| 0.7 * 2.5 | 62.9393 | 26.1856 | 8.7261 | 3.8348 | 1.2536 |
| 0.8 * 2.5 | 61.4415 | 25.0978 | 9.8830 | 1.9134 | 1.6643 |
| 0.9 * 2.5 | 62.2393 | 19.1167 | 10.4686 | 6.4146 | 1.7608 |
| 1.0 * 2.5 | 66.2778 | 18.5104 | 10.7274 | 3.0171 | 1.4674 |
| 1.0 * 2.0 | 61.0024 | 23.9888 | 10.2720 | 3.3732 | 1.3636 |
| 0.8 * 2.0 | 60.9676 | 25.7300 | 9.7197 | 1.9649 | 1.6178 |
| 0.8 * 2.5 | 61.4415 | 25.0978 | 9.8830 | 1.9134 | 1.6643 |
| 0.8 * 3.0 | 59.2089 | 22.3008 | 13.0370 | 4.1315 | 1.3217 |
| 0.8 * 3.5 | 53.6062 | 26.0824 | 15.1665 | 3.6939 | 1.4509 |
| 0.8 * 4.0 | 58.9138 | 26.2965 | 10.7274 | 2.4584 | 1.6039 |

4. Ethanol Fermentation of Radix Puerariae after Steam Explosion Treatment

Glucoamylase was added to the pre-treated Radix Puerariae in an amount of 65 U glucoamylase per gram of dry steam exploded Radix Puerariae. Saccharification was performed in 58° C. water bath for 30 min. The saccharified materials were cooled down to 30-35° C., and sterilized with UV for 15-20 min. Under sterile conditions, $(NH_4)_2SO_4$, $KH_2PO_4$ and an activated yeast were added, and continuous solid state fermentation was carried out to produce ethanol. The yield of ethanol, the contents of remaining reducing sugar and remaining total sugar in the fermented materials, as well as the amount of Radix Puerariae flavones extracted from the fermented materials were measured respectively. The results are shown in Table 4.

TABLE 4 the fermentation production of ethanol with steam exploded Radix Puerariae (based on fermented materials)

| Steam explosion condition | Water % in the materials | Ethanol % | Remaining reducing sugar % | Remaining total sugar % | Flavones % |
|---|---|---|---|---|---|
| 0.5 * 2.5 | 83.03 | 2.7689 | 0.3154 | 0.4823 | 0.2563 |
| 0.6 * 2.5 | 78.65 | 6.7419 | 0.4621 | 0.7657 | 0.2886 |
| 0.7 * 2.5 | 76.23 | 9.6271 | 0.4807 | 0.9352 | 0.5228 |
| 0.8 * 2.5 | 76.93 | 7.6180 | 0.5796 | 0.8812 | 0.6222 |
| 0.9 * 2.5 | 75.18 | 7.5576 | 0.6440 | 0.9128 | 0.6691 |
| 1.0 * 2.5 | 79.67 | 6.7267 | 0.3617 | 0.7720 | 0.6664 |
| 1.0 * 2.0 | 80.46 | 5.6391 | 0.4138 | 0.6180 | 0.5973 |
| 0.8 * 2.0 | 73.10 | 7.3159 | 0.4240 | 0.7651 | 0.5495 |
| 0.8 * 2.5 | 76.93 | 7.6180 | 0.5796 | 0.8812 | 0.6222 |
| 0.8 * 3.0 | 77.37 | 7.7751 | 0.4762 | 0.9318 | 0.8436 |
| 0.8 * 3.5 | 75.71 | 8.0108 | 0.3588 | 0.6622 | 0.8917 |
| 0.8 * 4.0 | 76.95 | 5.9563 | 0.4941 | 0.9881 | 1.0140 |

As shown in Table 4, the steam explosion pressure was raised from 0.5 MPa to 1.0 MPa, and also held for 2.5 min. The yield of ethanol in the fermented materials tended to first increase and then decrease. When fermentation was performed after the steam explosion treatment under 0.7 MPa and with a pressure holding time of 2.5 min, the yield of ethanol in the fermented materials was the highest, reaching 9.62%, whereas the yield of flavones in the fermented materials increased as the steam explosion pressure became larger. When the steam explosion pressure was maintained at 0.8 MPa, and the pressure holding time was extended from 2.0 min to 4.0 min, the effect of the variation in steam explosion pressure on the yield of ethanol and the amount of extracted flavones in the fermented materials was similar to the effect on Radix Puerariae fermentation. When fermentation was performed after the steam explosion treatment under 0.8 MPa and with a pressure holding time of 3.5 min, the yield of ethanol in the fermented materials could reach 8.01%; and the extraction rate of Radix Puerariae flavones reached 0.8917%. Regarding the yield of ethanol from the Radix Puerariae fermentation, as well as the amount of Radix Puerariae flavones extracted from the fermented materials, the optimized condition for pre-treating Radix Puerariae by low pressure steam explosion was 0.8 MPa and a pressure holding time of 3.5 min.

5. The Extraction of Flavones from the Fuel Ethanol Residues Obtained from Radix Puerariae Fermentation It can be seen in Table 4 that after Radix Puerariae was pre-treated by steam explosion under 0.8 MPa for a pressure holing time of 3.5 min, the amount of Radix Puerariae flavones extracted from the residues of the solid state fermentation for producing ethanol reached 0.8917% (based on the fermented materials). The water content of the fermented materials was 75.71%, whereas approximately 46 g dry materials were obtained after the fermentation of 100 g dry Radix Puerariae. Based on these, it was calculated that approximately 1.7 g flavones was extracted from the residues obtained from the fermentation of every 100 g dry Radix Puerariae, which maintained the same level as the amount of flavones extracted from the materials before fermentation. Radix Puerariae was extracted at the same time the ethanol was fermented.

6. The Classifying and Utilizing of the Radix Puerariae Fibers in the Fermentation Residues Ethanol fermentation was performed after the different parts of Radix Puerariae were pre-treated by steam explosion. The components of the fermentation residues were measured, and the results were shown in Table 5. The different parts of Radix Puerariae were subjected to ethanol fermentation, respectively. The content of raw fibers in the fermentation residues was 18.245~29.889%. The content of hemicellulose in the fermentation residues of Radix Puerariae was 52.154%, which was much higher than the contents of hemicellulose in the fermentation residues of other parts. However, the contents of hemicellulose in the fermentation residues of Radix Puerariae stalks and leafstalks were only 29.391% and 27.438%, respectively.

The fermentation residues (60-70%) were dried directly with hot air until the water content reached about 25%. Then two portions, i.e. fiber portion and protein powder portion were mechanically classified using ratchets. Among those, the fiber portion accounted for 70% of the total fermentation residues and its fiber length was measured as 2.4 mm at maximum, 0.75 mm at minimum, and 1.59 on average, so it is a nice raw material for making paper. The protein powder portion (short fiber portion) contained about 21.8% of protein, so it may be used as raw material for feedstuff.

TABLE 5 the component analysis of the fermentation residues from different parts of *Pueraria*

| | Neutral detergent % | Hemicellulose % | Raw fiber content % |
|---|---|---|---|
| Radix Puerariae | 16.625 | 52.154 | 18.245 |
| Radix Puerariae stalk | 16.776 | 29.391 | 29.889 |
| leafstalk | 20.291 | 27.438 | 29.198 |

7. Process and Embodiments

Based on above experimental results, we chose to co-produce ethanol and Radix Puerariae flavones as well as utilize Radix Puerariae fibers after pre-treating Radix Puerariae with low pressure steam explosion.

8. The Primary Features of the Process

Starting from the characteristics of Radix Puerariae, a graded transformation and a comprehensive and clean utilization of Radix Puerariae components were accomplished, with the features and merits shown below:

1) A Novel Steam Explosion Method for Radix Puerariae without Pollution

Radix Puerariae is pre-treated by means of a short-time (2-4 min) nonpolluting steam explosion technique. The heat mechanical chemical action of the steam explosion breaks cell walls of plant tissues, damages structures of the solid material i.e. Radix Puerariae, and raises the dextrinization rate of Radix Puerariae starch. The steam exploded Radix Puerariae can be fermented directly to produce fuel ethanol. The pre-treatment of Radix Puerariae with the steam explosion technique avoids a long-time steam boiling procedure (30-120 min) of the raw material starch, reduces the energy depleted in the fermentation for producing ethanol, shortens the period of production, and decreases the cost of production.

2) A Novel Method for Synchronously Saccharified Solid State Fermentation Radix Puerariae If the synchronously saccharified solid state fermentation is utilized to produce ethanol, only a small amount of water is required to be added, which dramatically lowers the water content in the fermented mash. Such method is used to reduce the energy depletion for distillation while increasing the ethanol content in the fermented mash, thereby cutting down the succeeding procedures for disposing water waste, providing conditions for reusing the fermentation residues while performing a clean production and reducing the production cost. So it benefits the comprehensive utilization of Radix Puerariae.

3) A Novel Technique for Co-Producing the Fuel Ethanol and Radix Puerariae Flavones The synchronously saccharified fermentation of Radix Puerariae to produce fuel ethanol is a process in which the structure of Radix Puerariae fibers is damaged, Radix Puerariae starch is released and the fuel ethanol is made from Radix Puerariae starch. If Radix Puerariae flavonoids are not extracted from the residues when the synchronously saccharified fermentating Radix Puerariae is used to produce the fuel ethanol, it not only causes resource waste, but also gives rise to environment issues. If Radix Puerariae flavones are extracted from the fermentation residues, Radix Puerariae will be utilized comprehensively, which boosts the economic effects and benefits the industrial production of Radix Puerariae.

4) A Method for Producing Ethanol by Continuous Solid State Fermentation

There is a problem that the Radix Puerariae solid state fermentation ethanol technique can not be carried out continuously. As such, the invention provides a method for performing the Radix Puerariae solid state fermentation ethanol using a continuous solid state fermentation device. A study of ethanol fermentation was carried out using the continuous solid state fermentation device shown in FIG. 2. Fermentation and separation were coupled in such a device, and $CO_2$ was used as a circulating carrier gas to separate the ethanol obtained by fermentation from the fermented materials. In this way, the effect of the heat generated during fermentation on the fermentation may be reduced on the one hand, and the inhibition of ethanol may be decreased on the other hand.

5) A Comprehensive Utilization of the Remaining Fermented Fibrous Residues

Because the novel process of solid state fermentation is used, the water content in the fermentation residues is very low (60-70%), which is suitable for the comprehensive utilization. Directly as feedstuff, the residues contain a low level of protein and a high level of raw fibers. Thereby a novel method for separating the fiber portion is developed. In such method, the mechanically separated fibers are used as raw material for making paper or fabric, whereas the solid powder residues having a high content of protein are used as protein feedstuff.

The results of the study indicate that the fiber content in the fermentation residues is approximately 18%. The fiber length of the fiber portion is measured, wherein the maximal length is 2.4 mm, the minimal length is 0.75 mm, and the average length is 1.59 mm, so the fiber portion is a nice raw material for making paper. The protein powder portion (short fiber portion) contains about 21.8% of protein, so it may be used as raw material for feedstuff.

6) A Novel Method for Fermenting the Remaining Fibrous Residues and Separating Protein Powder The fermentation residues (60-70%) are dried directly with hot air until the water content reaches about 25%. Then the two portions, i.e. the fiber portion and protein powder portion are mechanically classified using ratchets.

BRIEF DESCRIPTION OF THE DRAWINGS

FIG. 1 shows a process of a technical system for cleanly co-producing ethanol, Radix Puerariae flavones and Radix Puerariae fibers by way of steam explosion and solid state fermentation of Radix Puerariae.

FIG. 2 shows a device used in the continuous solid state fermentation.

EMBODIMENTS FOR CARRYING OUT THE INVENTION

Example 1

1. Steam explosion pre-treatment: Radix Puerariae was steam exploded under a steam pressure of 0.6 Mpa for 2.5 min;
2. Sterilization and inoculation: the steam exploded Radix Puerariae was placed in an antoclave and sterilized therein. The sterilization temperature was 121° C., and the sterilization time was 20 min. Steaming sterilization was used in the solid state fermentation reactor. Steam entered through the inlet 11 and exited through the outlet 12, maintaining at 121° C. for more than 30 min. After the sterilized materials was cooled down to 35° C., glucoamylase (90 U/g steam exploded dry materials), 0.1% $(NH_4)_2SO_4$, 0.1% $KH_2PO_4$ and 0.2% of activated yeast were added under sterile conditions;
3. Fermentation: after the motor of the airlock was turned on, the sterilely inoculated Radix Puerariae substrate was delivered slowly into the fermentation pot with a speed of 1 kg/10 h (the natural stacking density was approximately 400 g/L) through the feeding port 1. When the materials were fed for fermentation, $CO_2$ entered through the gas inlet 11 and replaced the air inside the pot. The temperature was maintained at 35±1° C. in the fermentation pot. The rotating speed of the screw was adjusted to ensure the residence time of the materials in the pot was about 60 h;
4. Gas extraction: while being fermented, Radix Puerariae substrate moved forward under the pushing action of the screw propeller and reached the gas extraction pot 3 right after 60 h. The gas was circulated by the $CO_2$ entering through the gas inlet 13 at the bottom of the gas extraction pot. The gas speed was 5 L/min, and ethanol was carried away from the substrate;
5. Adsorption: the mixed gas of $CO_2$ and ethanol passed two active carbon absorbing columns 4, 5 in parallel (two adsorbing columns were in parallel. If one adsorbing column was measured to reach saturation using an ethanol concentration meter 16, the other adsorbing column may then be switched to). The ethanol contained in the mixture was adsorbed, and the remaining $CO_2$ was compressed and may be utilized repeatedly;
6. Desorption: when no ethanol was measured in the mixed gas by using the ethanol concentration meter 16, the adsorbing column was heated to 90° C., permitting the adsorbed ethanol to be desorbed off the active carbon absorbing column;
7. Recovering by condensation: the ethanol desorbed off the adsorbing column was brought into a condensation tube 6 by the air flow entering through the bottom of the adsorbing column. The ethanol was recovered and obtained after the condensation;
8. Material Discharge: after fermentation, the Radix Puerariae residue was discharged through the discharging airlock 15 at the bottom of the gas extraction pot;
9. Filter pressing the fermentation residues for solid-liquid separation: the Radix Puerariae residues exited from the bottom of the gas extraction pot were filter pressed. The resultant solid residues and filtrate were kept separately for later use;
10. Extracting Radix Puerariae flavones: to the filtrate and solid residues obtained from step 9, 95% ethanol was added with a volume ratio of the filtrate to 95% ethanol to be 1:3.75, or absolute ethanol was added with a volume ratio of the filtrate to absolute ethanol to be 1:3.0. Standing for 2 h followed by centrifugal separation. Ethanol with a concentration of 75% was added to the solid residues with a mass/volume ratio of the solid residue to extraction solvent of 1:6. The extraction was performed for 2 times under reflux when heated to a temperature of 70° C. for a total extraction time of 3 h. The extracting liquid was filtered;
11. Purifying and refining Radix Puerariae flavones: the centrifugal supernatant in step 10 and the extracting liquid for extracting the solid residues were combined. Ethanol was recovered under a vacuum degree of −0.08 Mpa at a temperature of 50° C. The concentrated liquid was loaded onto a macroporous adsorbing resin. The macroporous adsorbing resin was eluted first with water to remove impurities and then with 50% ethanol to collect the ethanol eluent. After concentration, ethanol was added to render the alcohol concentration to reach 70%. The precipitate was filtered off. The filtrate was concentrated, and extracted by adding n-butanol. Then the n-butanol phase was recovered, concentrated, dried and the Radix Puerariae flavonoids extract was obtained.
12. The classification of Radix Puerariae fibrous residues: the fibrous residues obtained after the extraction of Radix Puerariae flavones under reflux in step 10 ; was directly hot-air dried until the water content reaches about 25%, followed by mechanically classifying into a fiber portion and a protein portion with a ratchet.

Based on the fermentation materials, the resultant ethanol accounted for 6.7419%; and Radix Puerariae flavones accounted for 0.2886%. In the fermentation residues, the content of Radix Puerariae fibers was 19.833%; and the protein content of the protein powder was 20.75%.

Example 2

1. Steam explosion pre-treatment: Radix Puerariae was steam exploded under a steam pressure of 0.8 Mpa for 3.5 min;
2. Sterilization and inoculation: the steam exploded Radix Puerariae was placed in an antoclave and sterilized therein. The sterilization temperature was 121° C., and the sterilization time was 20 min. Steaming sterilization was used in the solid state fermentation reactor. Steam entered through the inlet 11 and exited through the outlet 12, maintaining at 121° C. for more than 30 min. After the sterilized materials was cooled down to 30° C., glucoamylase (65 U/g steam exploded dry materials), 0.05% $(NH_4)_2SO_4$, 0.1% $KH_2PO_4$ and 0.25% of activated yeast were added under sterile conditions;
3. Fermentation: after the motor of the airlock was turned on, the sterilely inoculated Radix Puerariae substrate was delivered slowly into the fermentation pot with a speed of 1 kg/10 h (the natural stacking density was approximately 400 g/L) through the feeding port 1. When the materials were fed for fermentation, $CO_2$ entered through the gas inlet 11 and replaced the air inside the pot. The temperature was maintained at 35±1° C. in the fermentation pot. The rotating speed of the screw was adjusted to ensure the residence time of the materials in the pot was about 60 h;
4. Gas extraction: while being fermented, Radix Puerariae substrate moved forward under the pushing action of the screw propeller and reached the gas extraction pot 3 right after 60 h. The gas was circulated by the $CO_2$ entering through the gas inlet 13 at the bottom of the gas extraction pot. The gas speed was 4 L/min, and ethanol was carried away from the substrate;
5. Adsorption: the mixed gas of $CO_2$ and ethanol passed two active carbon absorbing columns 4, 5 in parallel (two adsorbing columns were in parallel. If one adsorbing column was measured to reach saturation using an ethanol concentration meter 16, the other adsorbing column may then be switched to). The ethanol contained in the mixture was adsorbed, and the remaining $CO_2$ was compressed and may be utilized repeatedly;
6. Desorption: when no ethanol was measured in the mixed gas by using the ethanol concentration meter 16, the adsorbing column was heated to 90° C., permitting the adsorbed ethanol to be desorbed off the active carbon absorbing column;
7. Recovering by condensation: the ethanol desorbed off the adsorbing column was brought into a condensation tube 6 by the air flow entering through the bottom of the adsorbing column. The ethanol was recovered and obtained after the condensation;

8. Material Discharge: after fermentation, the Radix Puerariae residue was discharged through the discharging airlock 15 at the bottom of the gas extraction pot;
9. Filter pressing the fermentation residues for solid-liquid separation: the Radix Puerariae residues exited from the bottom of the gas extraction pot were filter pressed. The resultant solid residues and filtrate were kept separately for later use;
10. Extracting Radix Puerariae flavones: to the filtrate and solid residues obtained from step 9, 95% ethanol was added with a volume ratio of the filtrate to 95% ethanol to be 1:2.8, or absolute ethanol was added with a volume ratio of the filtrate to absolute ethanol to be 1:2.3. Standing for 2 h followed by centrifugal separation. Ethanol with a concentration of 70% was added to the solid residues with a mass/volume ratio of the solid residue to extraction solvent of 1:8. The extraction was performed for 3 times under reflux when heated to a temperature of 75° C. for a total extraction time of 3 h. The extracting liquid was filtered;
11. Purifying and refining Radix Puerariae flavones: the centrifugal supernatant in step 10 and the extracting liquid for extracting the solid residues were combined. Ethanol was recovered under a vacuum degree of −0.08 Mpa at a temperature of 50° C. The concentrated liquid was loaded onto a macroporous adsorbing resin. The macroporous adsorbing resin was eluted first with water to remove impurities and then with 55% ethanol to collect the ethanol eluent. After concentration, ethanol was added to render the alcohol concentration to reach 75%. The precipitate was filtered off. The filtrate was concentrated, and extracted by adding n-butanol. Then the n-butanol phase was recovered, concentrated, dried and the Radix Puerariae flavonoids extract was obtained.
12. The classification of Radix Puerariae fibrous residues: the fibrous residues obtained after the extraction of Radix Puerariae flavones under reflux in step 10 was directly hot-air dried until the water content reaches about 25%, followed by mechanically classifying into a fiber portion and a protein portion with a ratchet.

Based on the fermentation materials, the resultant ethanol accounted for 8.0108%; and Radix Puerariae flavones accounted for 0.8917%. In the fermentation residues, the content of Radix Puerariae fibers was 21.711%; and the protein content of the protein powder was 19.27%.

The invention claimed is:

1. A process for comprehensively utilizing Radix Puerariae, comprising:
provSiding Radix Puerariae as raw material;
pretreating the Radix Puerariae raw material by steam explosion;
producing and separating ethanol by continuous coupled solid state fermentation of the pretreated Radix Puerariae raw material;
filtering off a fermentation residue from the fermented Radix Puerariae raw material to obtain a filtrate; and
extracting and purifying Radix Puerariae flavones from the filtrate.

2. The process for comprehensively utilizing Radix Puerariae according to claim 1, further comprising:
separating the filtered fermentation residue into a fiber portion and a protein portion.

3. The process for comprehensively utilizing Radix Puerariae according to claim 1, wherein in said pretreating, the steam pressure is 0.5 to 1.0 MPa, and the steam explosion time is 2 to 4 minutes.

4. The process for comprehensively utilizing Radix Puerariae according to claim 1, wherein in said producing and separating, glucoamylase, $(NH_4)_2SO_4$, $KH_2PO_4$ and activated yeast are added for the fermentation of the pretreated Radix Puerariae raw material.

5. The process for comprehensively utilizing Radix Puerariae according to claim 4, wherein the added amount of said glucoamylase is 50~100 U/g of the pretreated Radix Puerariae raw material; the added amount of said $(NH_4)_2SO_4$ is 0.05~0.15 g/100 g of the pretreated Radix Puerariae raw material; the added amount of said $KH_2PO_4$ is 0.05~0.2 g/100 g of the pretreated Radix Puerariae raw material; and the added amount of said activated yeast is 0.10~0.30 g yeast/100 g of the pretreated Radix Puerariae raw material.

6. The process according to claim 1, wherein in said extracting and purifying, model D-101, DS-401 or AB-8 macroporous adsorbing resin is used to remove impurities.

7. The process according to claim 1, wherein said continuous coupled solid state fermentation comprises:
providing a device comprising an airlock, a screw, a horizontal pot, a vertical pot; a gas inlet and a gas outlet of said horizontal pot, a discharging airlock of said vertical pot, and a gas inlet and a gas outlet of said vertical pot;
providing the pretreated Radix Puerariae raw material to said horizontal pot through said airlock;
slowly propelling said screw inside said horizontal pot to move the provided pretreated Radix Puerariae raw material towards said vertical pot; and
continuously discharging the material present in said vertical pot through said airlock at the bottom of said vertical pot,
wherein a biochemical process selected from the group consisting of enzymolysis, fermentation and separation of the pretreated Radix Puerariae raw material is performed to completion.

8. The process according to claim 7, wherein the pretreated Radix Puerariae raw material is subjected to enzymolysis.

9. The process according to claim 7, wherein the pretreated Radix Puerariae raw material is subjected to fermentation.

* * * * *